United States Patent [19]
Aranyi

[11] Patent Number: 5,483,952
[45] Date of Patent: Jan. 16, 1996

[54] HANDLE FOR SURGICAL INSTRUMENTS

[75] Inventor: Ernie Aranyi, Easton, Conn.

[73] Assignee: United States Surgical Corporation, Norwalk, Conn.

[21] Appl. No.: 196,886

[22] Filed: Feb. 15, 1994

Related U.S. Application Data

[63] Continuation of Ser. No. 765,993, Sep. 26, 1991, abandoned.

[51] Int. Cl.$^6$ .............................. A61B 1/00; A61B 17/00
[52] U.S. Cl. ...................... 600/131; 606/205; 606/206; 128/751
[58] Field of Search ...................................... 606/205, 206, 606/207, 208, 209, 210, 211, 26, 51, 52, 83; 128/4, 7, 751; 604/61

[56] References Cited

U.S. PATENT DOCUMENTS

| | | |
|---|---|---|
| 1,310,982 | 7/1919 | Davis . |
| 1,452,373 | 4/1923 | Gomez . |
| 1,606,497 | 11/1926 | Berger . |
| 1,659,112 | 2/1928 | Littlejohn . |
| 2,269,963 | 1/1942 | Wappler ........................... 604/61 |
| 2,363,334 | 11/1944 | Jones . |
| 3,470,872 | 10/1969 | Grieshaber ..................... 606/207 X |
| 3,746,002 | 7/1973 | Haller . |
| 3,807,406 | 4/1974 | Rafferty et al. . |
| 3,964,468 | 6/1976 | Schulz . |
| 3,989,033 | 11/1976 | Halpern et al. ................. 606/206 X |
| 4,043,323 | 8/1977 | Komiya . |
| 4,049,002 | 9/1977 | Kletschka et al. . |
| 4,411,653 | 10/1983 | Razi . |
| 4,428,374 | 1/1984 | Auburn . |
| 4,572,185 | 2/1986 | Rich . |
| 4,611,595 | 9/1986 | Klieman et al. . |
| 4,614,187 | 9/1986 | Mulhollan et al. . |
| 4,643,190 | 2/1987 | Heimberger . |
| 4,662,371 | 5/1987 | Whipple et al. . |
| 4,669,647 | 6/1987 | Storace . |
| 4,712,545 | 12/1987 | Honkanen . |
| 4,813,407 | 3/1989 | Vogen . |
| 4,872,456 | 10/1989 | Hasson ........................... 606/207 |
| 4,896,661 | 1/1990 | Bogert et al. . |
| 4,935,027 | 6/1990 | Yoon . |
| 4,950,273 | 8/1990 | Briggs . |
| 4,994,065 | 2/1991 | Gibbs et al. . |
| 5,009,661 | 4/1991 | Michelson . |
| 5,174,300 | 12/1992 | Bales et al. ........................ 128/751 |
| 5,176,699 | 1/1993 | Markham ....................... 606/208 X |
| 5,176,702 | 1/1993 | Bales et al. . |
| 5,217,460 | 6/1993 | Knoepfler ...................... 606/208 X |

FOREIGN PATENT DOCUMENTS

| | | |
|---|---|---|
| 0065054 | 8/1981 | European Pat. Off. . |
| 0240722 | 10/1987 | European Pat. Off. . |
| 0392547 | 10/1990 | European Pat. Off. . |
| 0392548 | 10/1990 | European Pat. Off. . |
| 2542188 | 9/1984 | France . |
| 220437 | 4/1961 | Germany . |
| 8311392 | 4/1983 | Germany . |
| 9106506 | 9/1991 | Germany . |
| 2044108 | 3/1980 | United Kingdom . |

OTHER PUBLICATIONS

Padgett Instruments Bulletin.
Solos Endoscopy Brochure.

*Primary Examiner*—Richard J. Apley
*Assistant Examiner*—Beverly M. Flanagan

[57] ABSTRACT

An endoscopic or laparoscopic surgical instrument having an internally disposed ratchet mechanism located within a barrel portion of a handle assembly. The instrument includes a handle assembly having a pivoting handle and a stationary handle, a barrel portion to which an elongated body assembly is secured, and a ratchet mechanism for releasably positioning a tool mechanism located at the distal end of the body assembly at various increments. The ratchet mechanism comprises a pawl member and a rack member which are disposed within the handle assembly. A rotational knob and locking member may also be provided to lock the body assembly at various orientations to the longitudinal axis.

58 Claims, 18 Drawing Sheets

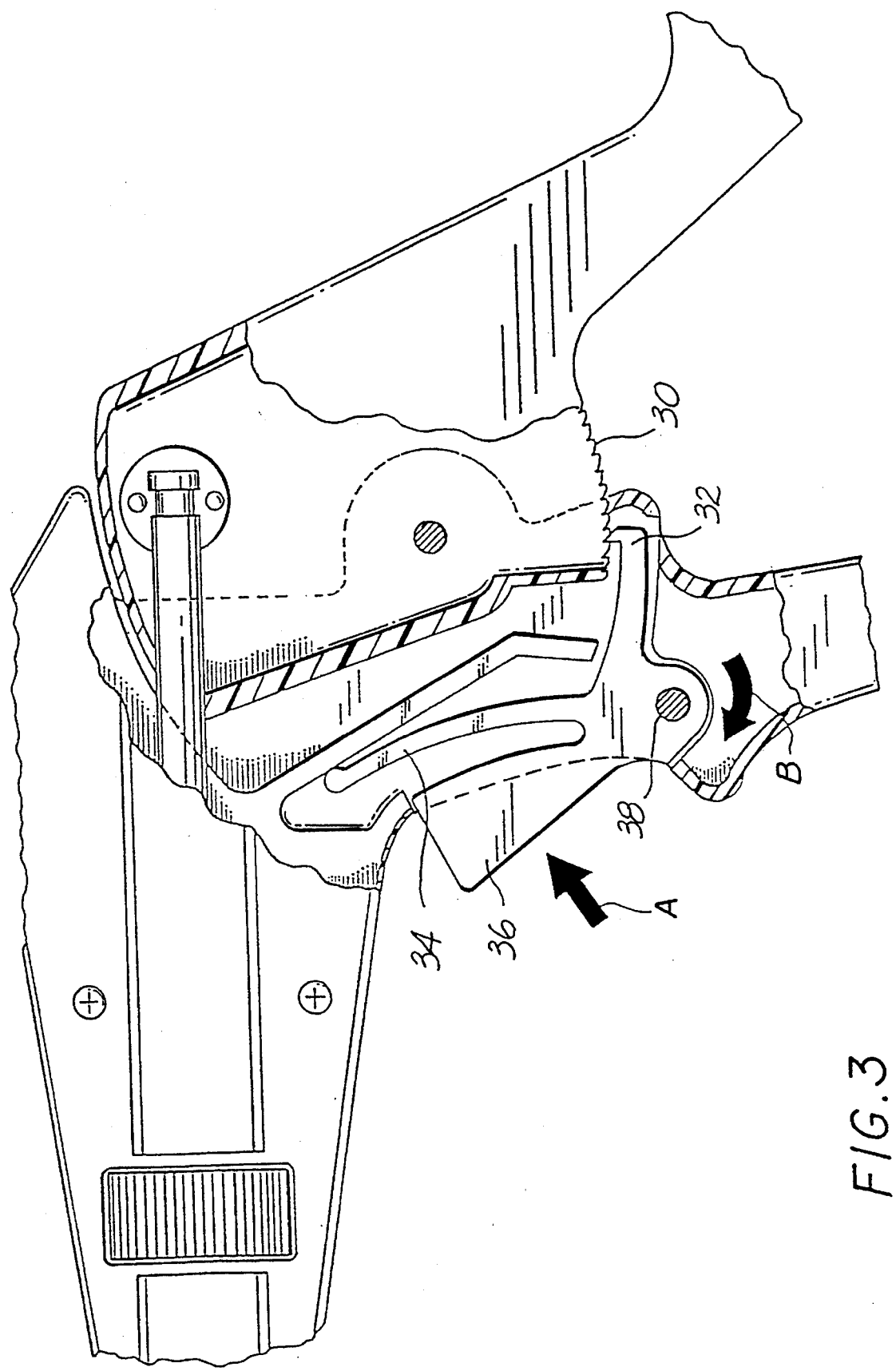

2

HANDLE FOR SURGICAL INSTRUMENTS

This is a continuation, of U.S. application Ser. No. 07/765,993 filed on Sep. 26, 1991, abandoned.

BACKGROUND OF THE INVENTION

1. Field of the Invention

The present invention relates to surgical instruments, and more particularly relates to a handle for an endoscopic or laparoscopic surgical instrument having reciprocating jaw members which pivot in response to the opening and closing of the handle members, where movement of the handle members is translated through an elongated tubular body member to open and close the jaw mechanism. The present invention further relates to a ratchet mechanism which is internally disposed within the handle to provide incremental positioning of the jaw members in relation to each other.

2. Discussion of the Prior Art

In the prior art, various endoscopic surgical instruments are disclosed which utilize generally complex mechanisms for opening and closing handle members and jaw members to facilitate use of the device at a surgical site. Many devices provide an intricate construction in which a linkage mechanism for opening and closing the jaws requires numerous moving parts, while a sliding arrangement is provided between two extended rod members to activate the linkage mechanism in response to movement of the handle members. In addition, pivoting of the handle members in many cases causes an unwanted radial torquing force on the rod which requires additional space to be provided in the handle members to accommodate the radial movement of the rod.

Furthermore, it is often necessary for the surgeon, or an assistant, to maintain a constant force on the handles to keep the jaw mechanism closed in the event that the instrument is a grasping or gripping device such as forceps, needle holders, or retractors. This limits the surgeon's range, and in the case of an assistant, often requires additional personnel to be present in the operating room, thus restricting movement in an already confining location. To alleviate this problem, it has been known to provide locking mechanisms on the handles of the surgical instruments which allow the surgeon to lock or clamp the jaw members in place to free his hands to operate additional instruments during the course of the operation. Furthermore, this frees the surgical assistant to support the surgeon and eliminates the need for additional assistants. Typical locking devices include arm members which extend between the handles so that a series of ridges or ribs on each arm member engage corresponding ridges on the opposite arm to lock the handles in position. Bending one arm in relation to the other releases the locking mechanism.

A disadvantage associated with these devices concerns the release of the locking mechanism for subsequent movement of the jaw members to remove or reposition the instrument. Generally, the arm members of locking mechanisms are constructed of a resilient material, such as stainless steel or rigid plastic, and the locking forces which hold the arm members in engagement are generated by the natural flexing and biasing of the material of which the arm members are constructed. To release the locking mechanism, the arms must be disengaged by overcoming the locking forces of the arms. Typically, this is accomplished by manually flexing the arms away from each other, necessitating the use of two hands, one to grasp the instrument, and the other to forcibly move the arm members. This, of course, requires the surgeon (or assistant) to cease what he is doing and release the mechanism, thus reducing the effectiveness of the surgeon during the operation, particularly in an emergency situation.

A further disadvantage lies in the fact that typical locking mechanisms cannot be overridden; that is, the mechanism is always engaged, thereby preventing free movement of the handle and jaw mechanism. This usually requires the surgeon to choose an instrument either having the locking mechanism or one that does not. This leads to an overabundance of instruments in the operating room and tends to complicate an already complex situation.

Finally, locking mechanisms located on the handles require special care in sterilization, packaging and storage, as well as in normal handling in the operating room. Dirt and debris may clog the ribs of the locking mechanism thus reducing its effectiveness, and damage to the ribs during storage or packaging may destroy the ribs, rendering the locking mechanism useless.

U.S. Pat. No. 1,452,373 to Gomez discloses a typical locking mechanism for a surgical instrument, in which a plurality of ribs are provided on an extension of the handle member which engage a similar rib member on the opposite handle. Once engaged, the handles must be moved away from each other perpendicular to their longitudinal axis to disengage the locking mechanism to release the jaw mechanism.

U.S. Pat. No. 4,896,661 to Bogert et al. disclose a surgical instrument having a ratchet mechanism positioned on the handle members which includes a curved rack member attached to one handle member which passes through a slot in the other handle member. A releasable pawl member is provided on the second handle to engage the rack member and provide a means for releasing the ratchet.

U.S. Pat. No. 4,935,027 to Yoon discloses a surgical instrument having a ratchet mechanism positioned between the handle members. A rack member is provided which extends from one handle and passes through a slot in the second handle to lock the handles in place. Pivoting the rack member away from corresponding grooves in the slot will release the ratchet mechanism.

U.S. Pat. No. 4,428,374 to Auburn discloses a surgical instrument having means for positioning and holding the handle members in relation to each other. A rack member is provided on one handle member which extends through a slot in the second handle member in which a releasable pawl mechanism is provided to engage and disengage the ratcheting mechanism.

The novel surgical instrument pursuant to the present invention obviates the disadvantages encountered in the prior art and provides a precise instrument which is easy to manufacture and efficient to use, which eliminates many of the moving parts required by prior art devices. The instrument of the present invention incorporates many features which are of use to the surgeon during an operation, including an internal ratcheting mechanism to provide for incremental movement of the tool mechanism and locking of the jaws if desired, while maintaining a lightweight construction in an easy to handle device in which all of the features may be operated with one hand. Furthermore, the features are so positioned so as to provide a maximum line of sight for the surgeon without obstructing the view to the surgical site.

SUMMARY OF THE INVENTION

The present invention provides a novel endoscopic or laparoscopic surgical device which incorporates many features necessary for endoscopic or laparoscopic surgical procedures, and provides a lightweight and easy to use device which may be operated with one hand. The device includes an internal ratcheting mechanism located preferably within the barrel of the handle mechanism which provides for incremental positioning of the tool mechanism for performing the surgical procedure. The device is simple to manufacture, and may incorporate any one of a series of jaw mechanisms for various surgical procedures. The device is a high precision instrument in which many moving parts normally associated with such a device are eliminated, thus reducing instances of mechanical failure requiring expensive repair or ultimate destruction of the instrument.

The endoscopic or laparoscopic surgical instrument of the present invention essentially consists of a handle assembly, an elongated body assembly, and a ratchet mechanism attached within the barrel portion of the handle assembly. The handle assembly includes a stationary handle and pivoting handle, attached to the barrel portion, and the body assembly is attached to the barrel portion and extends therefrom. The body assembly consists of an outer tubular member and an inner rod member which coaxially passes within the outer tubular member. The rod member is attached to the pivoting handle, while the tube member is secured in a conventional manner to the barrel portion which extends into the stationary handle. As the pivoting handle moves, the rod member slidably reciprocates within the outer tube member.

Attached to a distal end of the body assembly is the tool mechanism which opens and closes in response to movement of the pivoting handle in relation to the stationary handle. The tool mechanism may comprise a pair of jaw members wherein one or both jaw members open and close to perform various endoscopic or laparoscopic surgical procedures. The jaw mechanism includes, but is not limited to, a scissor device, a dissecting device, a grasping device, a retractor device, and like mechanisms.

The present invention also includes the provision of a second pivot point on the pivoting handle, to which the inner rod member is attached. As the handle pivots, the second pivot point rotates to allow the inner rod to move longitudinally in the outer tube with minimal radial deflection. This feature reduces the radial wear on the inner rod and prevents weakening of the structure during long term use. In addition, it allows for a reduction of the required internal spacing between the outer tube and inner rod to result in a more compact and streamlined instrument. Furthermore, unwanted torquing forces are eliminated at the pivot point thus minimizing the possibility of mechanical breakdown of the instrument at the connection between the pivoting handle and the movable inner rod.

The present invention also includes the provision of a rotatable knob on the outer tubular member to allow the body assembly and jaw mechanism to rotate to position the jaws at desired angles to the longitudinal axis during the surgical procedure. Preferably, the rotatable knob is secured to the outer tube and positioned in a slot which passes through the barrel portion of the stationary handle, so that a surgeon may rotate the knob, and consequently the body assembly and jaw mechanism, through the use of his thumb while he is holding the stationary handle with his fingers. This frees the surgeon's other hand to simultaneously operate another instrument during surgery.

A novel feature of the present invention is the provision of a ratchet mechanism located internally within the barrel of the handle assembly to provide for incremental movement of the jaw mechanism. Since it is located internally within the barrel portion of the handle assembly, it is not subjected to environmental conditions which may result in clogging or damage to the ratchet mechanism during handling and storage. Furthermore, the novel ratchet mechanism of the present invention provides for simple handling and maneuvering during the surgical procedure and allows the surgeon to operate the device with one hand, thus freeing his other hand for performing other functions during the surgical procedure.

The ratchet mechanism of the present invention includes a trigger mechanism for engaging and disengaging the ratchet feature. In a first embodiment, a rack member is provided on the surface of the pivoting handle which engages the pawl arm of the trigger portion of the ratchet mechanism. The pawl arm is biased by a leaf spring member which maintains the pawl arm in contact with the rack member. The trigger member, when depressed, overcomes the force of the leaf spring and pivots the pawl arm away from the rack member to release the ratchet mechanism. If the trigger mechanism is continually pressed, the ratchet mechanism is overridden and the device functions as a conventional surgical instrument. The trigger mechanism is preferably positioned on the barrel portion of the stationary handle member. The rack member consists of a plurality of indentations or notches into which the pawl arm fits to secure the handles in incremental positions during operation of the tool mechanism.

A second embodiment of the ratchet mechanism of the present invention provides the trigger mechanism positioned on the stationary handle at the barrel portion and includes a pawl arm which engages a rack member which is constructed integral with the inner rod member of the body assembly. The rack member may comprise a plurality of indentations cut into the rod member which engage the pawl arm of the trigger mechanism. The trigger mechanism is spring biased so that the pawl arm is continually engaged with the rack member. Constant depression of the trigger mechanism overrides the ratchet mechanism and the handles may be operated as in a conventional tool.

Alternately, the indentations may be part of a block device which is secured to the rod member and provided with the plurality of indentations or notches to engage the pawl arm. Preferably, however, the notches or indentations are constructed integral with the rod member, and in a preferred embodiment are provided as a series of circumferential notches about the rod member. This allows for the provision of a rotatable body assembly through the use of a rotation knob which provides 360°, or any portion thereof, rotation of the body assembly to rotate the jaws of the tool mechanism to desired angles along the longitudinal axis of the instrument during the surgical procedure. Accordingly, the ratchet mechanism may operate at any orientation of the jaw members.

In order to provide a complete override feature of the ratchet mechanism, the present invention includes a novel actuator device which cooperates with the trigger mechanism to provide an on/off mechanism for the ratchet feature. In this embodiment, the trigger mechanism includes an articulated body portion having a projection or finger-like member which acts as a camming member to engage the actuator means. The actuator means essentially comprises a pivotable camming member having a slot into which the finger-like projection extends. When pivoted in a first direction, the camming slot engages the camming member of the articulated body and causes the body to pivot into engagement with the circumferential rack disposed on the inner rod member. When the actuator means is pivoted in a second direction, the camming slot is of such a configuration so as to disengage with the camming member of the articulated body which causes the pawl arm to fall out of engagement with the rack means of the inner rod member. In this embodiment, the trigger mechanism is also spring biased so that when the actuator means is in the "on" position, the pawl arm is biased into engagement with the rack means.

A further feature of the present invention is the provision of a stop mechanism to arrest rotation of the body assembly. The stop mechanism is provided in conjunction with the rotation knob and allows the surgeon to lock the body assembly at a particular orientation during rotation. The lock mechanism is provided on the barrel portion of the handle assembly and is positioned so that the surgeon may activate the lock mechanism with a single hand.

The present invention may also feature a connection port to provide the device with electrocautery capabilities. A connection port allows for the connection of a suitable jack member to be inserted into the device. The outer tube of the body assembly is provided with electrical insulation, preferably heat shrink tubing, which extends a substantial portion of the length of the outer tube. In this embodiment, the handle is molded of plastic material to provide electrical insulation for the user.

In the preferred embodiment, all the above features are incorporated into a single endoscopic and laparoscopic surgical instrument, so that the instrument has electrocautery, rotational, and ratcheting capabilities. However, the instrument of the present invention is constructed with at least the ratcheting capabilities to provide for incremental adjustment of the tool mechanism during a surgical procedure.

Accordingly, it is an object of the present invention to provide an endoscopic or laparoscopic surgical instrument in which all the features may be used by a surgeon with one hand.

It is another object of the present invention to provide an endoscopic or laparoscopic surgical instrument having ratcheting capabilities in which the ratchet mechanism is located internal of the handle assembly of the device.

It is a further object of the present invention to provide an endoscopic or laparoscopic surgical instrument in which the ratcheting mechanism may be overridden to allow for full movement of the handles of the device.

It is still a further object of the present invention to provide an endoscopic or laparoscopic surgical instrument in which a ratchet mechanism is provided along with a rotational body assembly so that the ratchet mechanism may be operated at any orientation of the tool mechanism.

BRIEF DESCRIPTION OF THE DRAWINGS

The foregoing objects and other features of the invention will become more readily apparent and may be understood by referring to the following detailed description of an illustrative embodiment of the endoscopic or laparoscopic surgical instrument having an internal ratchet mechanism, taken in conjunction with the accompanying drawings, in which:

FIG. 3 illustrates an exploded side cut-away view of the device of FIG. 2 showing in detail the ratchet mechanism according to the present invention;

DETAILED DESCRIPTION OF THE PREFERRED EMBODIMENTS

Figure 1:
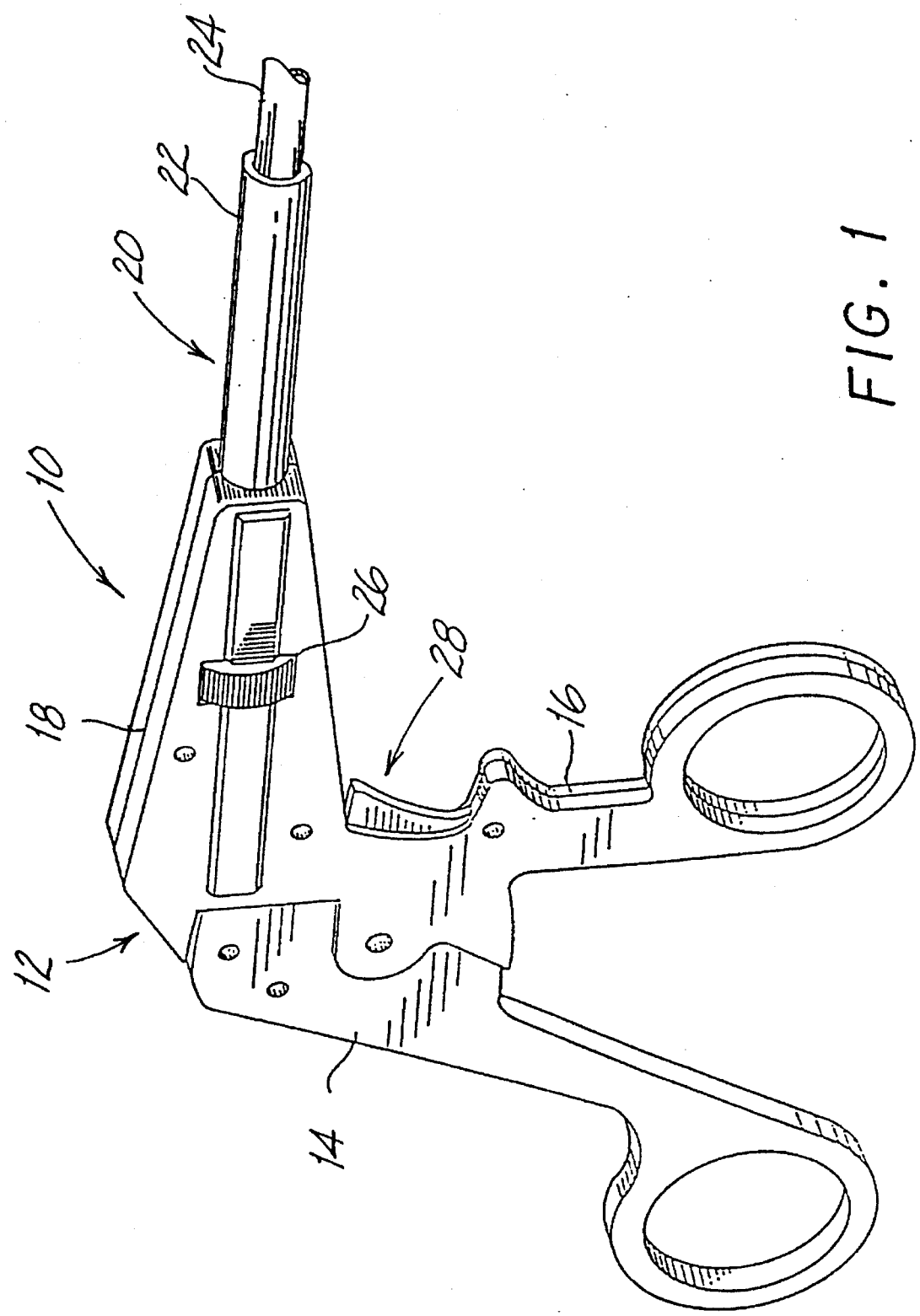
FIG. 1 illustrates a perspective view of an endoscopic or laparoscopic surgical instrument possessing the ratchet mechanism according to a first embodiment of the present invention.

Referring now in specific detail to the drawings, in which like reference numerals identify similar or identical elements, FIG. 1 illustrates a first embodiment of the endoscopic or laparoscopic surgical instrument 10. In its simplest form, device 10 comprises a handle assembly 12, a body assembly 20, and a ratchet mechanism 28. Handle assembly 12 comprises a pivoting handle 14, a stationary handle 16, and a barrel portion 18 to which body assembly 20 is attached. Body assembly 20 essentially comprises an outer tubular member 22 through which an inner rod member 24 coaxially passes in a slidable arrangement. Preferably, outer tube 22 is secured to barrel portion 18 and remains stationary during operation of the device. Upon movement of pivoting handle 14, inner rod 24 reciprocates within tube member 22 to operate a tool mechanism provided at the distal end of the instrument 10. This tool mechanism (not shown) may comprise a surgical implement, such as scissors, graspers, forceps, retractors and the like. A rotation knob 26 may be provided which rotates body assembly 20 to orient the tool mechanism at various angles to the longitudinal axis.

Figure 2:
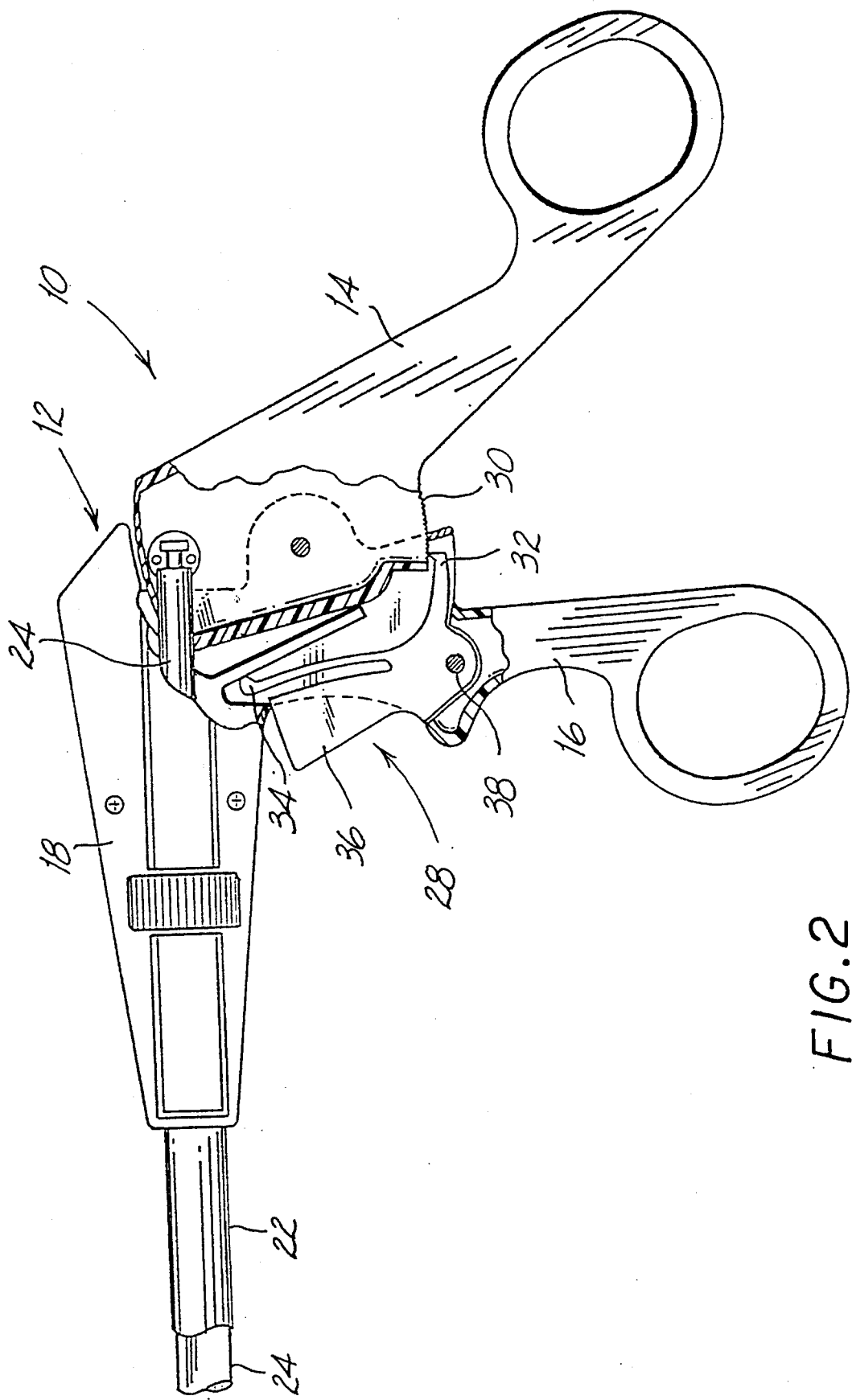
FIG. 2 illustrates a side plan view and partial cut-away of the surgical instrument of FIG. 1.

As best seen in FIGS. 2 and 3, ratchet mechanism 28 is provided to incrementally adjust and hold the position of pivoting handle 14. This incremental positioning, which sets pivoting handle 14 at various locations along its path of travel, provides a means to incrementally open and close the tool mechanism during the surgical procedure. Ratchet mechanism 28 is essentially positioned internally within barrel portion 18 and stationary handle 16 so that none of the mechanism is exposed to environmental conditions.

Figure 5:
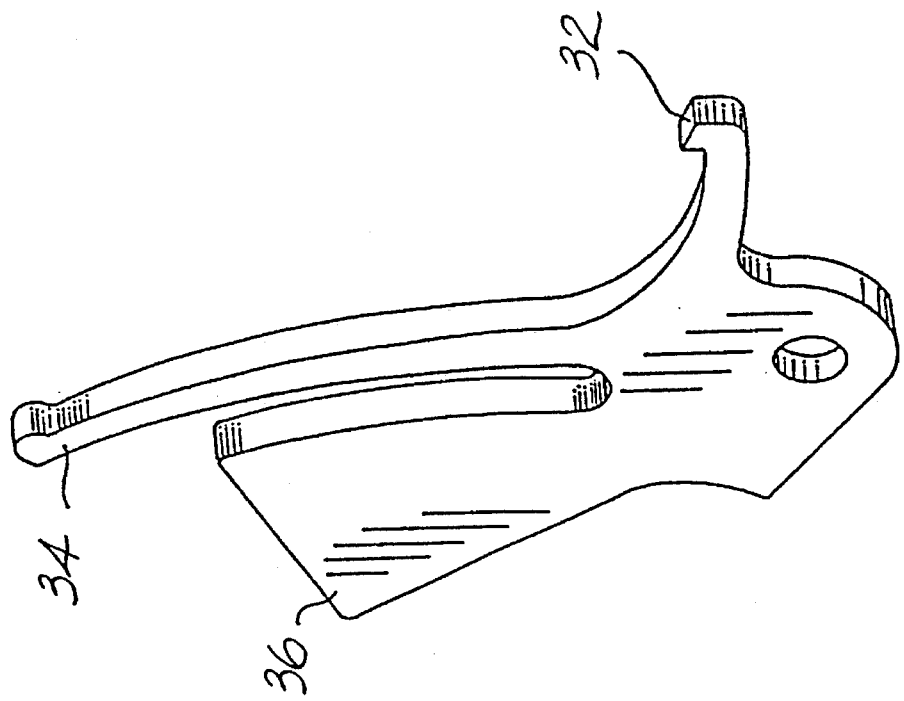
FIGS. 4 and 5 illustrate a side plan view and a perspective view, respectively, of the ratchet mechanism of the embodiment of FIG. 1.
Figure 4:
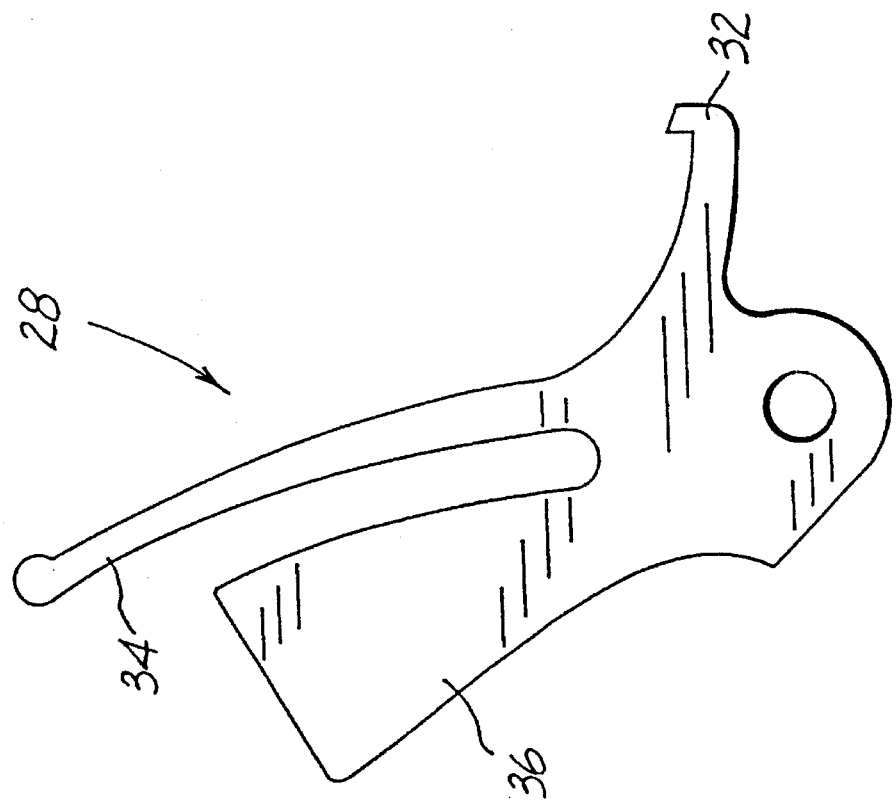

Ratchet mechanism 28 includes a pawl member 32 which engages a rack member 30 which is located on the pivoting handle 14. Rack member 30 comprises a plurality of indentations or notches which accepts pawl arm 32 to hold pivoting arm 14 in place. Ratchet mechanism 28 utilizes an integrally constructed leaf spring member 34 which biases ratchet mechanism 28 into the engaged position such that pawl member 32 engages rack member 30. To release the ratchet mechanism, a trigger member 36 is provided which, when depressed by the user in the direction of arrow A in FIG. 3, causes the ratchet mechanism 28 to pivot about pivot point 38 in the direction of arrow B to disengage pawl member 32 from rack member 30. It can be appreciated that continual depression of trigger member 36 in the direction of arrow A allows the ratchet mechanism 28 to be overridden so that pivoting handle 14 may operate freely without the constraints of ratchet mechanism 28. Releasing trigger member 36 will return the pawl member 32 to the engaged position. Ratchet mechanism 28 can be best seen in FIGS. 4 and 5.

Figure 6:
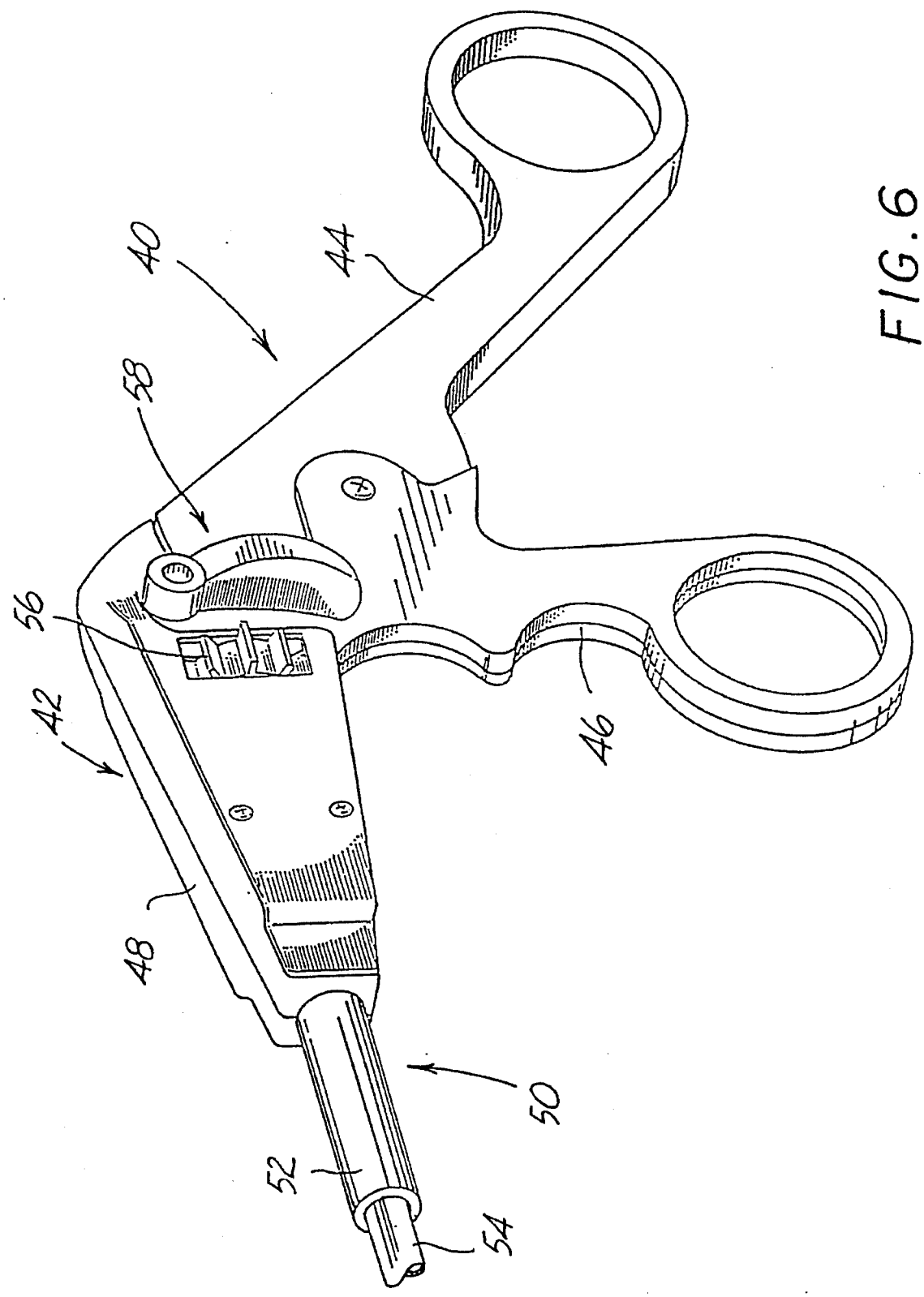
FIG. 6 illustrates a perspective view of an alternate embodiment of the endoscopic or laparoscopic surgical instrument employing the ratchet mechanism of the present invention.

FIG. 6 illustrates a second embodiment of the surgical instrument employing the ratchet mechanism of the present invention. Instrument 40 is similar to instrument 10 described above and includes a handle portion 42 to which body assembly 50 is attached. Body assembly 50 terminates in a tool mechanism similar to that described above.

Figure 7:
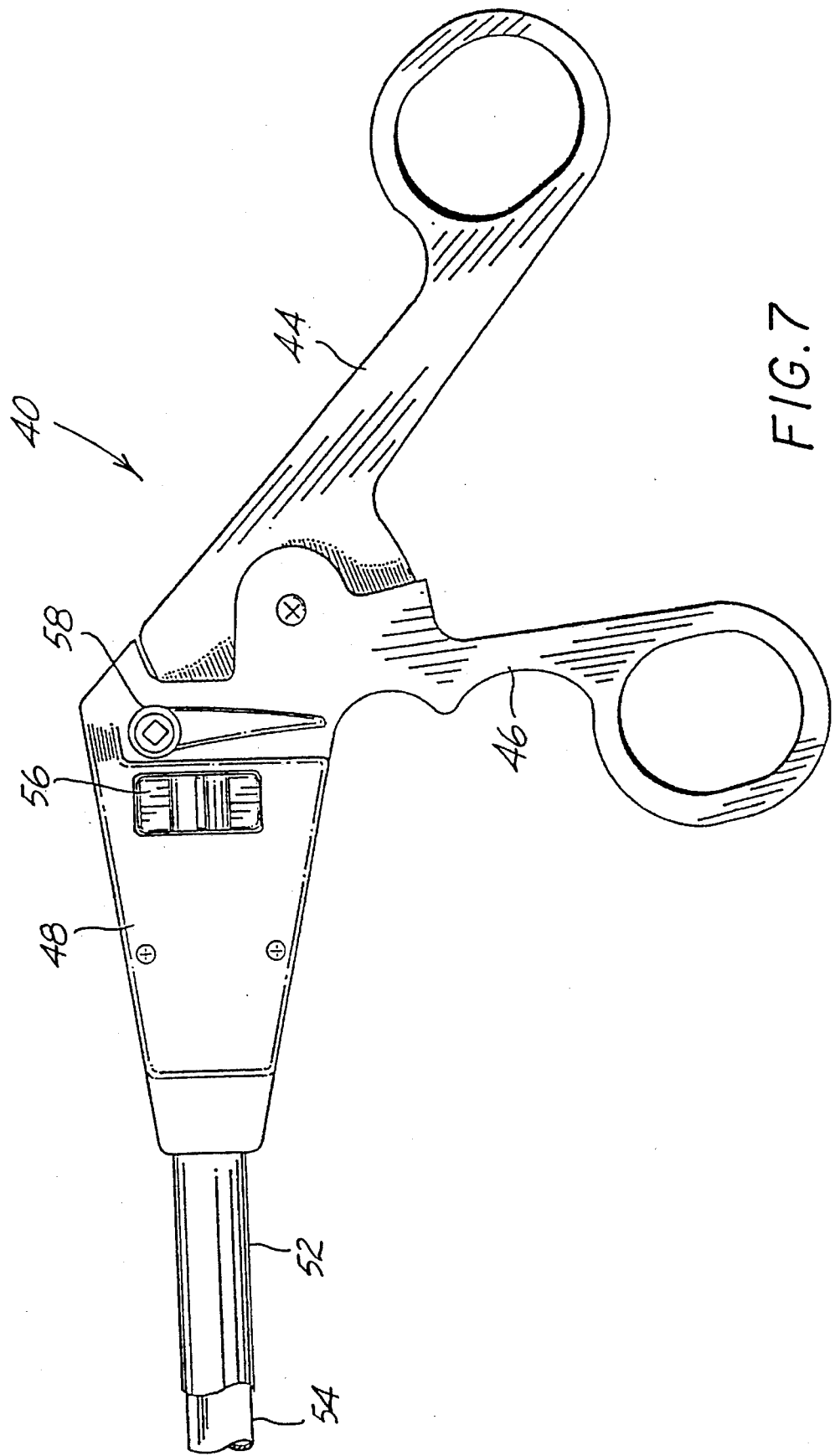
FIG. 7 illustrates a side plan view of the laparoscopic surgical instrument of FIG. 6.
Figure 8:
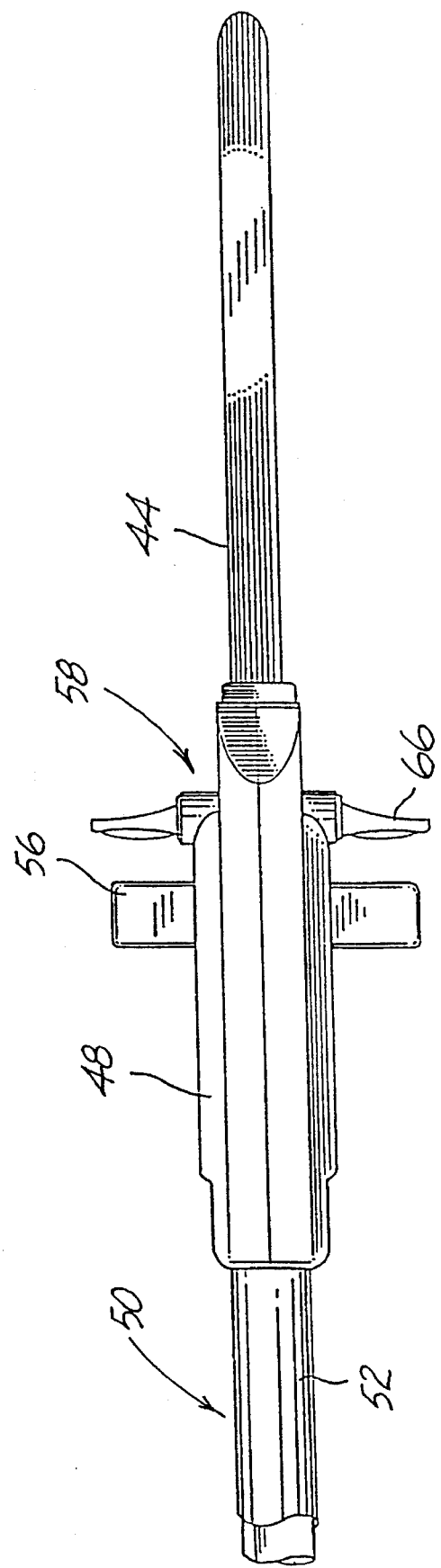
FIG. 8 illustrates a top plan view of the device of FIG. 6.

Handle assembly 42 comprises a pivoting handle 44, a stationary handle 46 and a barrel portion 48. Body assembly 50 comprises an outer tubular member 52 through which an inner rod member 54 coaxially passes in sliding arrangement. Movement of pivoting handle 44 causes inner rod member 54 to reciprocate within outer tube 52. Outer tube 52 is secured within barrel portion 48. As can be seen in FIG. 6 and FIG. 7, a rotation knob 56 may be provided, along with ratchet mechanism 58.

Figure 9:
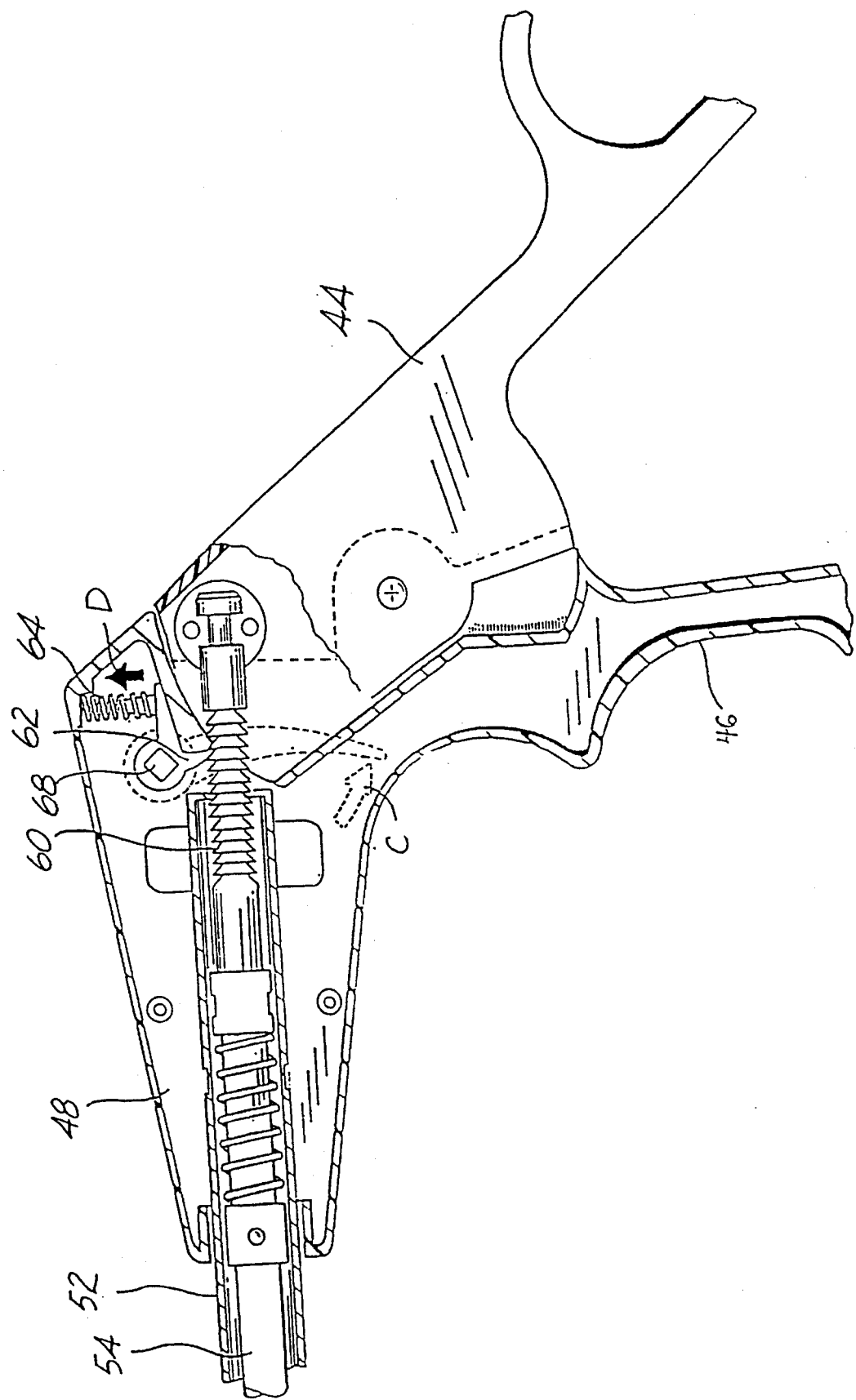
FIG. 9 illustrates a side cut-away view of the endoscopic or laparoscopic surgical instrument of FIG. 6 having the ratchet mechanism of the present invention.

FIG. 9 illustrates a cut-away view of the device of FIG. 6. Inner rod member 54 includes a rack member 60 which comprises a plurality of circumferential notches cut into rod member 54. The circumferential notches allow for activation of the ratchet mechanism at any orientation of the body assembly 50 due to rotation of rotation knob 56. While it is shown that rod member 54 contains the circumferential notches or indentations, a separate block member may be provided to which rod member 54 is attached to accomplish the same ratcheting principle.

Engaging rack member 60 is a pawl member 62 which is part of ratchet mechanism 58. Pawl member 62 is biased into the engaged position by spring 64, and is pivotable about pivot point 68.

In use, pivoting handle 44 is moved to open and close the jaw members of the tool mechanism (not shown). As pivoting handle 44 moves, pawl member 62 moves along rack member 60 to a desired location for the tool mechanism. To release ratchet mechanism 58, trigger member 66 is moved in the direction of phantom arrow C to overcome the spring force and move the pawl mechanism in the direction of arrow D. Once this mechanism is released, handle 44 is free to move without obstruction. In order to override the ratcheting mechanism, trigger member 66 may be continually depressed in the direction of phantom arrow C so that the pivoting handle 44 may operate freely.

Figure 10:
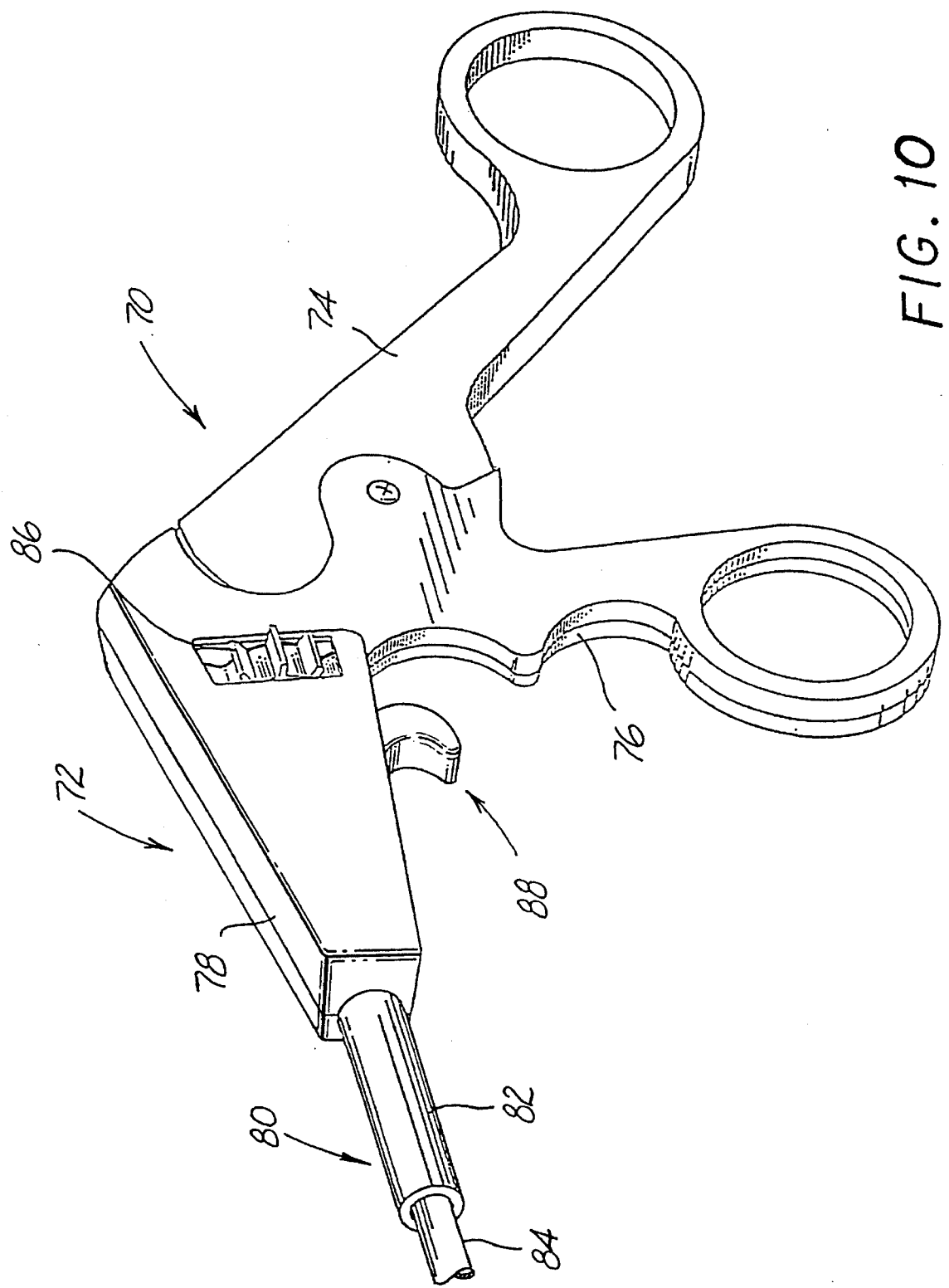
FIG. 10 illustrates a further embodiment of the endoscopic or laparoscopic surgical instrument employing the ratchet mechanism of the present invention.
Figure 11:
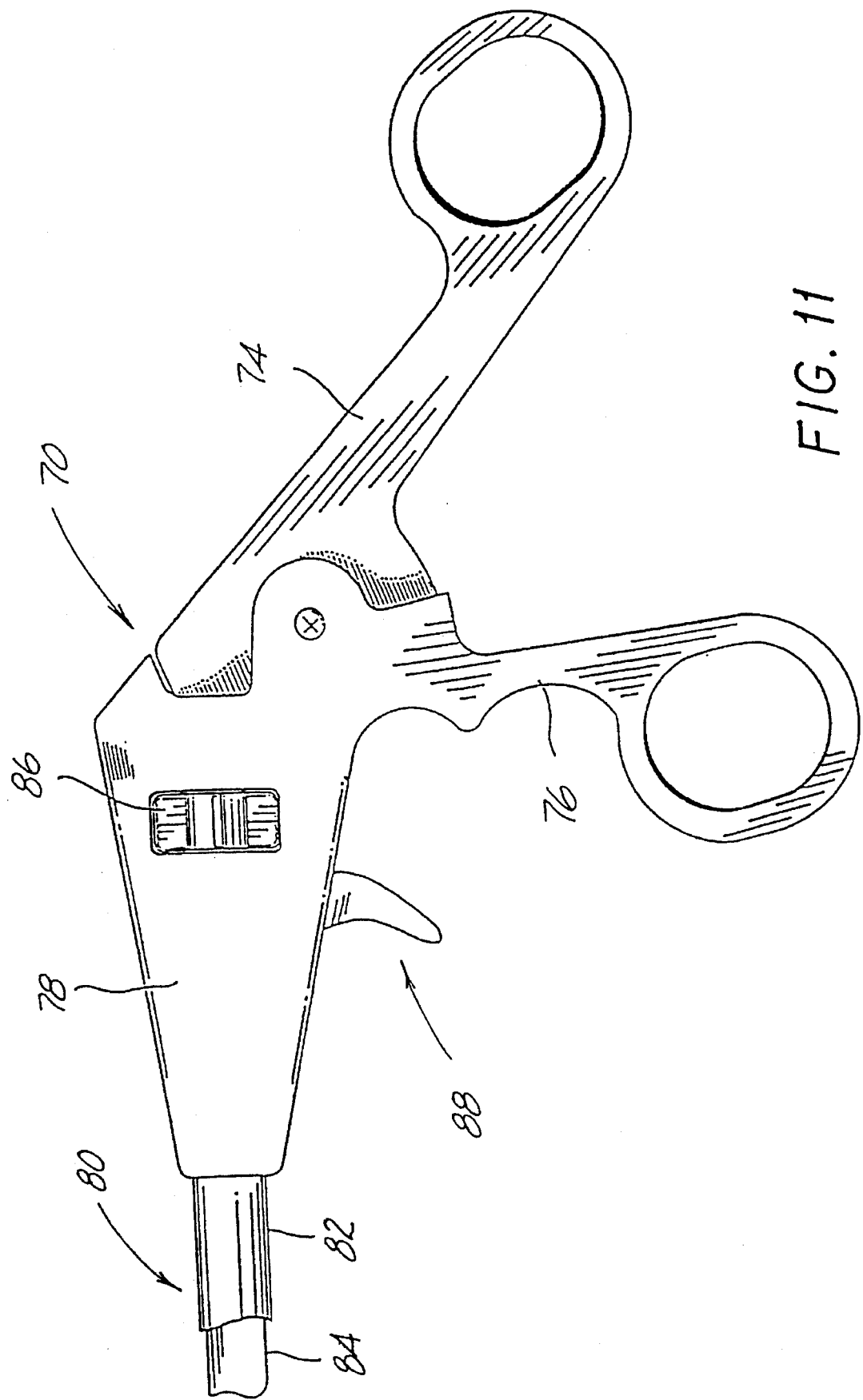
FIG. 11 illustrates a side view of the device of FIG. 10.

FIG. 10 illustrates a third embodiment of the endoscopic or laparoscopic surgical instrument employing the ratchet mechanism of the present invention. Instrument 70 is similar to devices 10 and 40 above and includes a handle assembly 72 and a body assembly 80. Body assembly 80 terminates in a tool mechanism similar to that described above. Handle assembly 72 includes a pivoting handle 74, a stationary handle 76 and a barrel portion 78. Body assembly 80 includes an outer tube member 82 which is secured to barrel portion 78, and an inner rod member 84 which coaxially passes through outer tube member 82 in sliding arrangement. Inner rod 84 reciprocates within outer tube member 82 upon movement of pivoting handle 74. A rotation knob 86 may be provided, and ratchet mechanism 88 is provided as a trigger grip extending from barrel portion 78.

Figure 12:
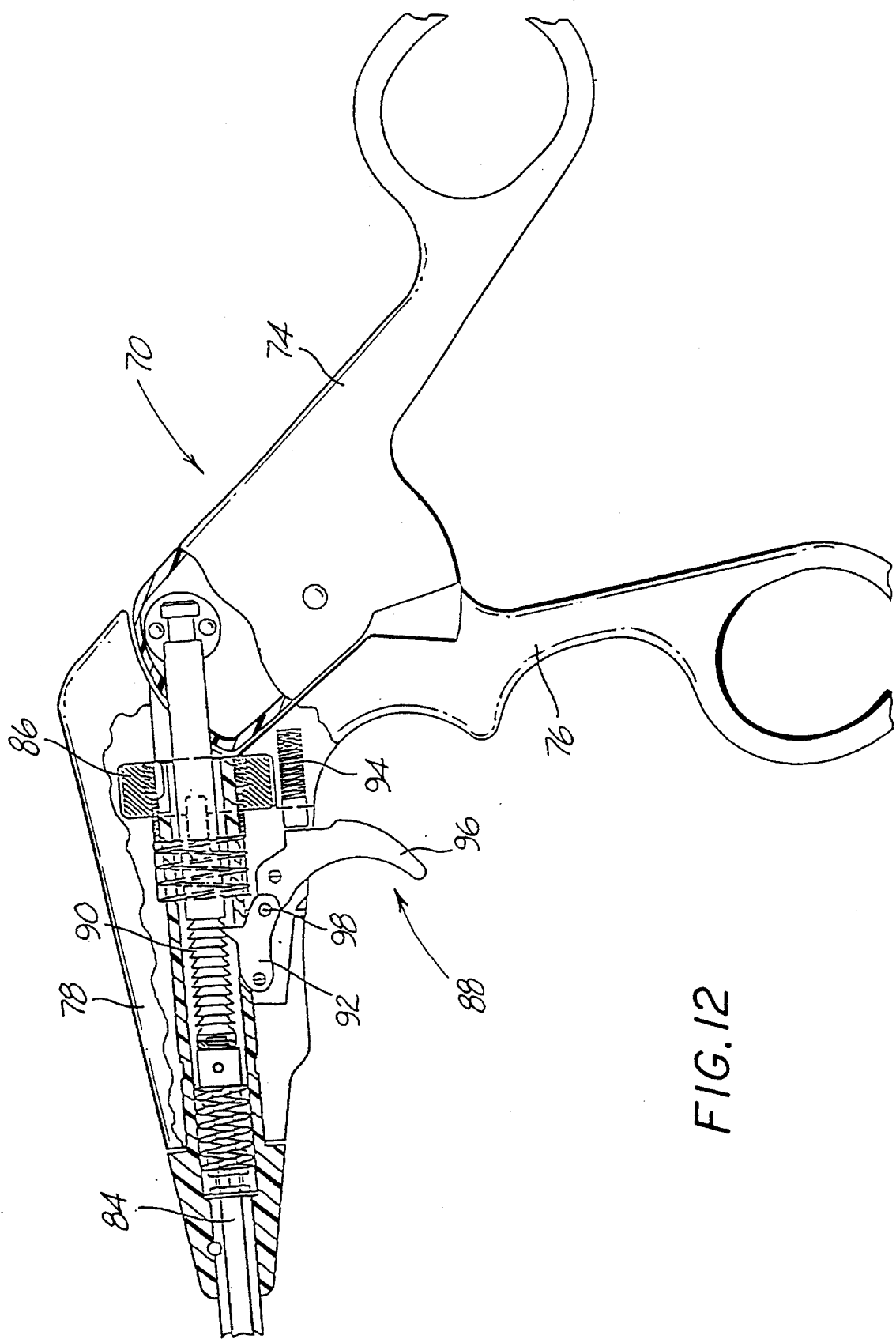
FIG. 12 illustrates a side cut-away view of the device of FIG. 10.

Turning to FIG. 12, there is illustrated the ratchet mechanism 88 which is disposed within barrel portion 78. A rack member 90 is provided which comprises a plurality of circumferential notches or indentations in inner rod member 84 which provide for engagement of the ratchet mechanism 88 regardless of the orientation of the tool mechanism due to rotation of rotation knob 86.

In this embodiment, ratchet mechanism 88 essentially comprises an articulated body which is comprised of pawl member 92 and trigger member 96. Trigger member 96 is biased by spring 94 which maintains pawl member 92 in engagement with rack member 90. The articulated body is formed about floating pivot point 98 which joins pawl member 92 with trigger member 96. Both the pawl member 92 and trigger member 96 are each secured at stationary pivot points while floating pivot point 98 allows pawl member 92 to move into and out of engagement with rack member 90.

In use, pivoting handle 74 is moved to set the jaws of the tool mechanism (not shown) to the desired configuration. Spring member 94 biases trigger member 96 forwardly, so that floating pivot point 98 urges pawl member 92 into engagement with rack means 90. To release the ratchet mechanism, trigger member 96 is urged rearwardly against the biasing force of spring 94 so that floating pivot point 98 shifts downwardly to move pawl member 92 out of engagement with rack means 90. Maintaining this rearward depression of trigger member 96 will provide an override for the ratchet mechanism 88, and allow pivoting handle 74 to move freely.

Figure 13:
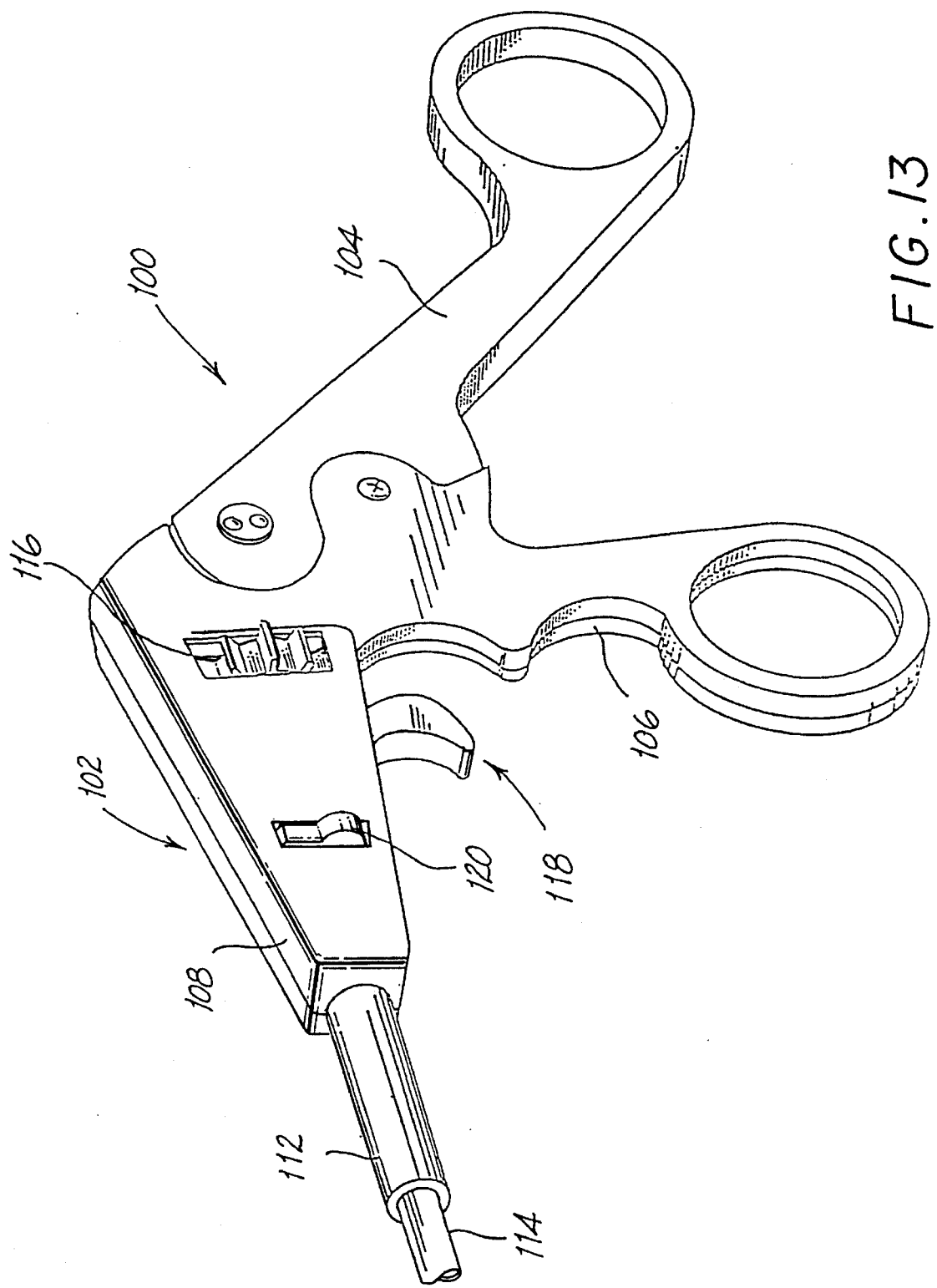
FIG. 13 illustrates another embodiment of the endoscopic or laparoscopic surgical instrument employing the ratchet mechanism of the present invention.

FIG. 13 illustrates a fourth embodiment of the endoscopic or laparoscopic surgical instrument 100 employing the ratchet mechanism of the present invention. Instrument 100 is similar to instruments 10, 40 and 70 above, and includes a handle assembly 102, a body assembly 110, and a ratchet mechanism 118. Handle assembly 102 comprises a pivoting handle 104, a stationary handle 106 and a barrel portion 108, to which body assembly 110 is secured. Body assembly 110 comprises an outer tubular member 112 and a coaxial inner rod member 114 which slides therein. Outer tube member 112 is secured to barrel portion 108, while inner rod member 114 is secured to pivoting handle 104 and reciprocates within outer tube member 112 upon movement of pivoting handle 104. A rotation knob 116 is provided to adjust the orientation of the tool mechanism (not shown) which is located at the distal end of the body assembly 110. Ratchet mechanism 118 is provided, along with actuation means 120, whose function will be described below.

Figure 15:
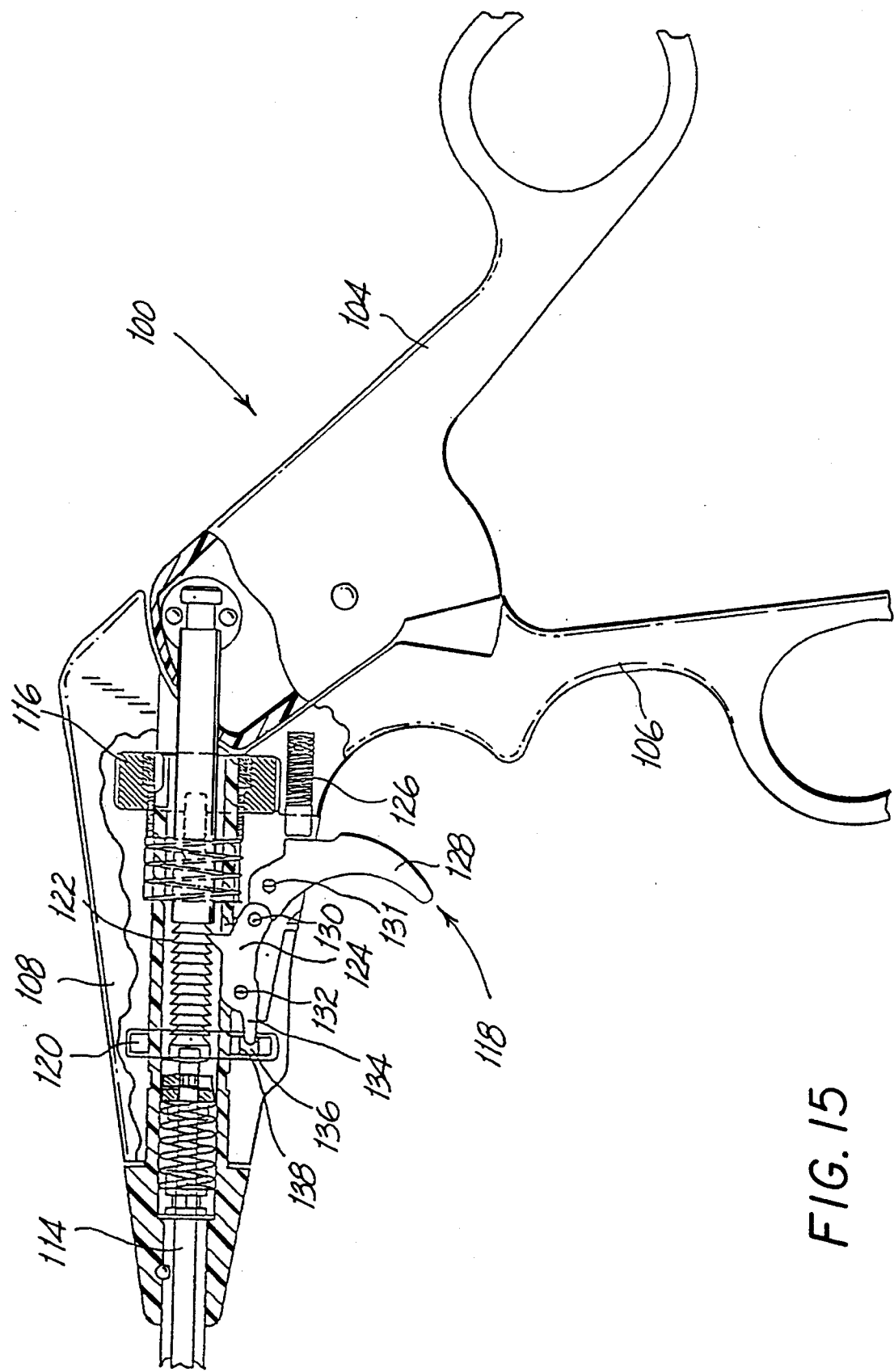
FIG. 15 illustrates a side cut-away view of the device of FIG. 13.

Turning now to FIG. 15, there is illustrated a side cutaway view of instrument 100 showing the ratchet mechanism 118 of the present invention. Inner rod member 114 includes a rack member 122 which comprises a plurality of circumferential notches or indentations which allows for use of the ratchet mechanism 118 regardless of the orientation of the tool mechanism due to rotation of body assembly 110 by rotation knob 116. Ratchet mechanism 118 comprises an articulated body which is formed by pawl member 124, trigger member 128 and a camming member 134 which extends from pawl member 124. Trigger member 128 pivots about a stationary pivot point 131 and is biased in the forward direction by spring 126. Trigger member 128 is joined to pawl member 124 through floating pivot point 130, while pawl member 124 is pivoted further about stationary pivot point 132.

Figure 19:
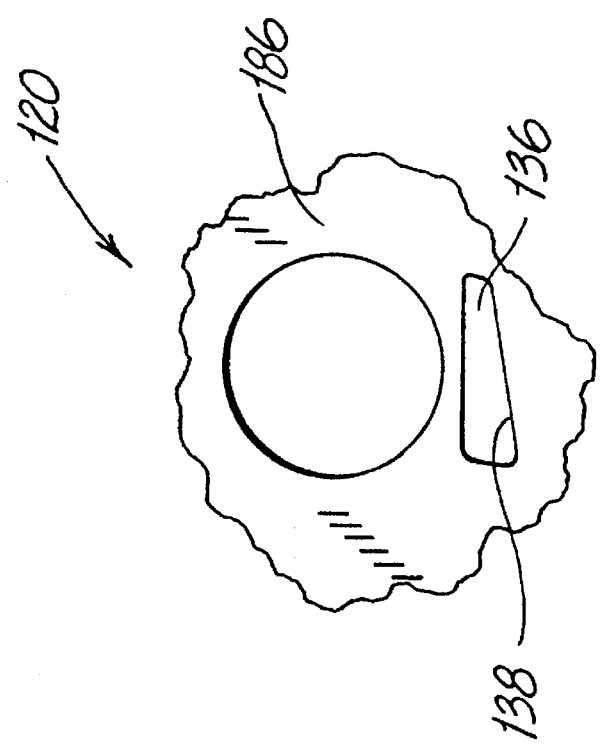
FIG. 19 illustrates a plan view of an embodiment of the actuation means for use with the ratchet mechanism of the present invention.

An actuation means 120 is provided, which is best seen in FIG. 19. Actuation means 120 comprises a body portion 186 and is provided with a camming slot 136 into which camming member 134 passes. Camming surface 138 engages camming member 134 to urge pawl member 124 into engagement with rack member 122. When actuation means 120 is pushed in a first direction, camming member 134 disengages from camming surface 138 and pawl member 124 disengages from rack member 122. When actuation means 120 is pushed in the opposite direction, camming surface 138 contacts camming member 134 which urges pawl member 124 into engagement with rack member 122. Actuation means 120 functions as a switch to the user to override the ratchet mechanism so that the device 100 may be used in a conventional manner without requiring the user to hold any component of the instrument.

Figure 14:
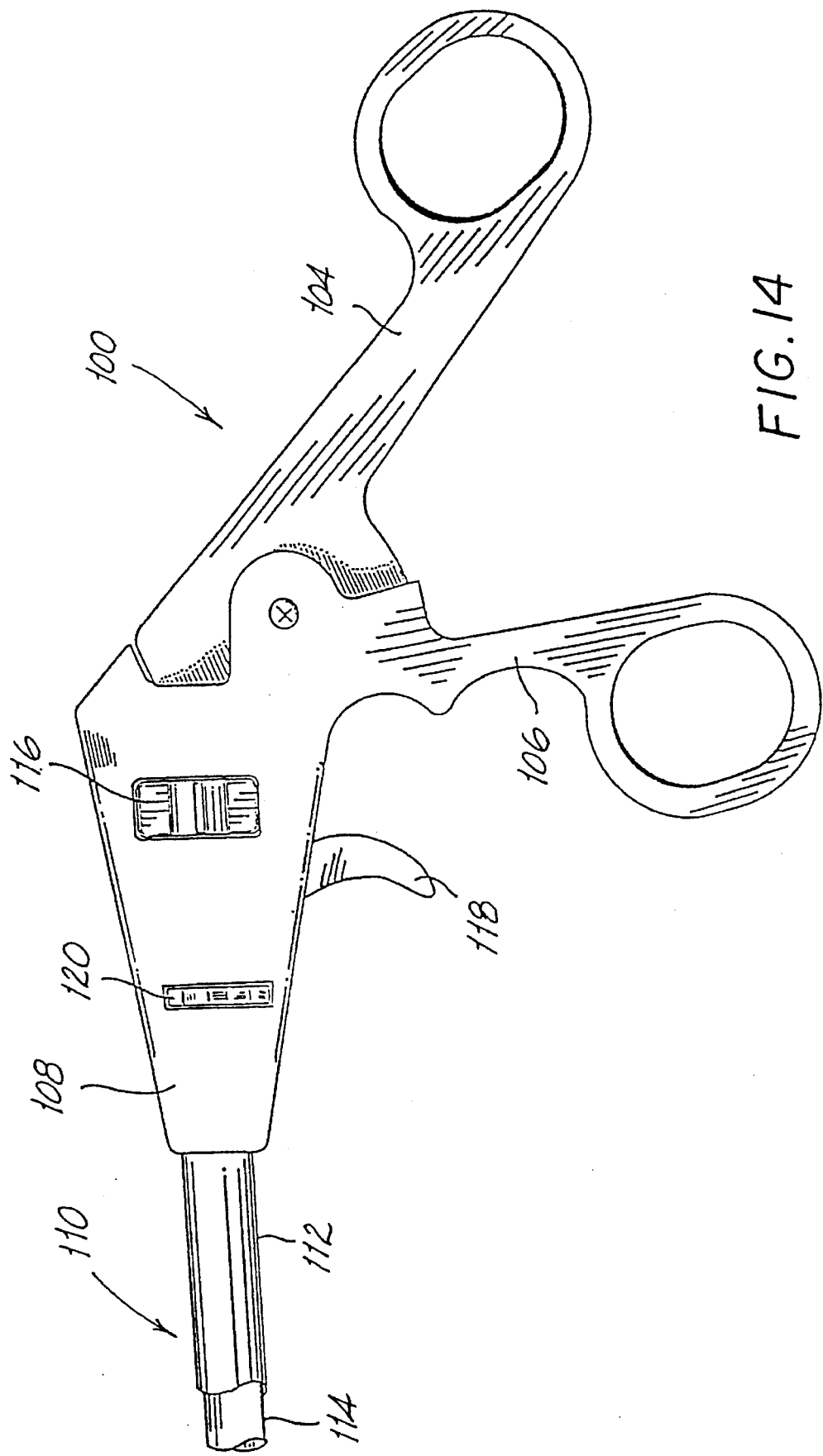
FIG. 14 illustrates a side plan view of the device of FIG. 13.
Figure 16:
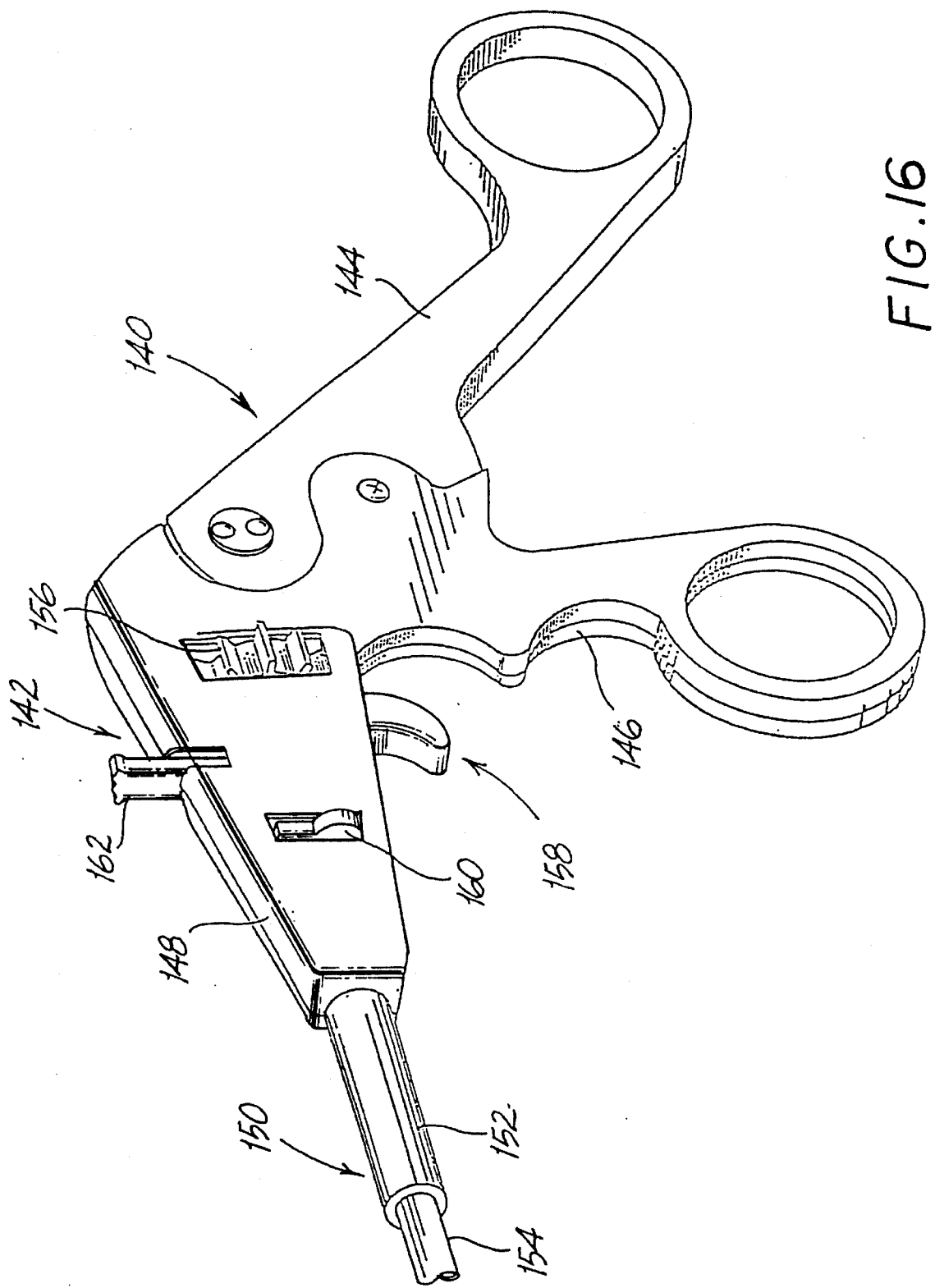
FIG. 16 illustrates a perspective view of a further embodiment of the endoscopic or laparoscopic surgical instrument employing the ratchet mechanism of the present invention.
Figure 17:
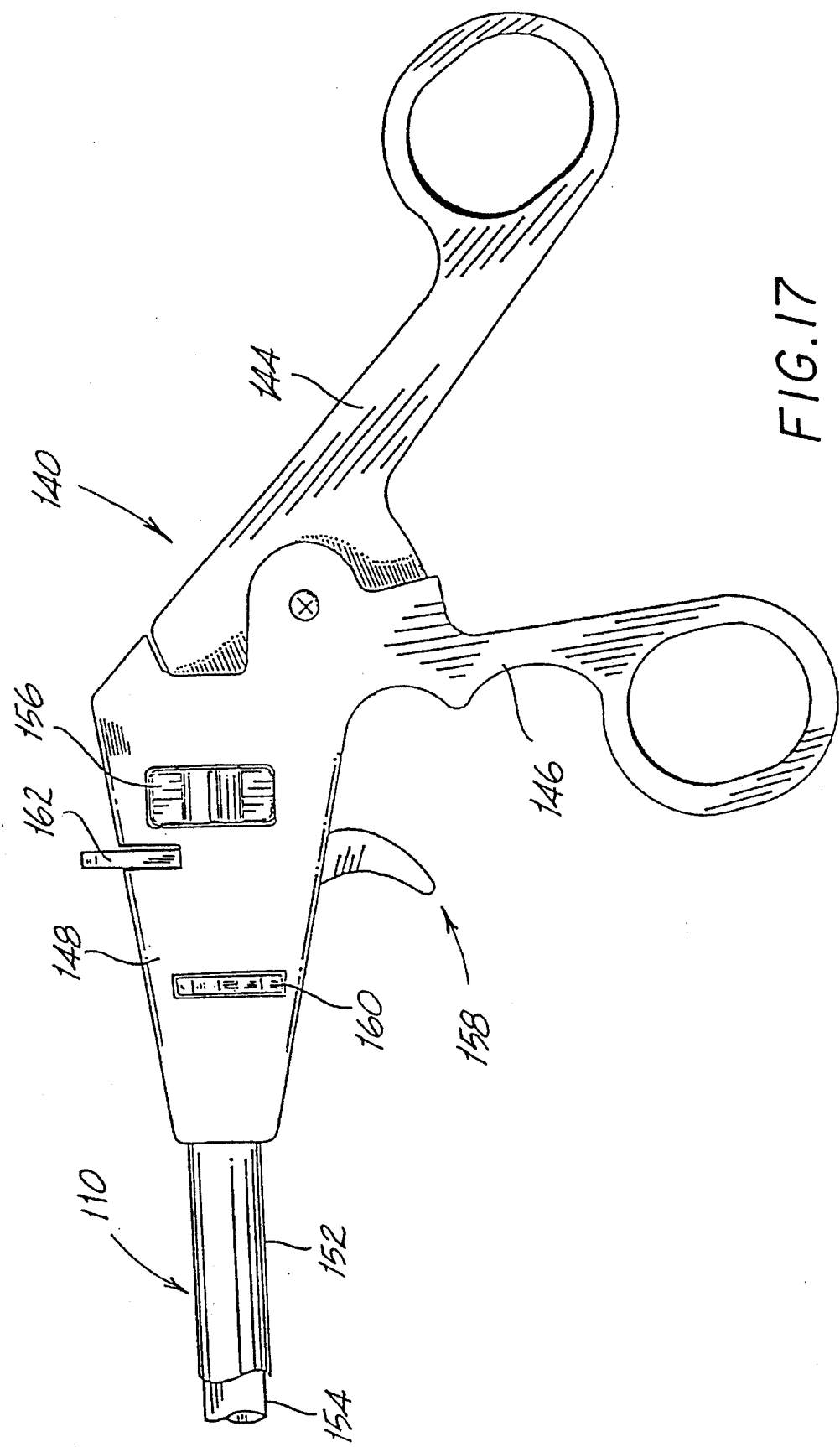
FIG. 17 illustrates a side plan view of the device of FIG. 16.

FIG. 16 illustrates a fifth embodiment of the endoscopic or laparoscopic surgical instrument 140 employing the ratchet mechanism of the present invention. Device 140 is identical to device 100 described above in relation to FIGS. 13–15, except for the provision of rotation stop means 162.

Instrument 140 comprises handle assembly 142, body assembly 150, and ratchet mechanism 158. Handle assembly 142 comprises pivoting handle 144, stationary handle 146, and barrel portion 148. Body assembly 150 attaches to barrel portion 148 in the manner described above, such that outer tube member 152 is secured to barrel portion 158 while inner rod member 154 slidingly passes through tube member 152 and is secured to pivoting handle 144. Inner rod member 154 reciprocates within outer tube member 152 in response to movement of pivoting handle 144. A rotation knob 156 is provided, along with actuation means 160 which cooperates with ratchet mechanism 158 as described above.

Figure 18:
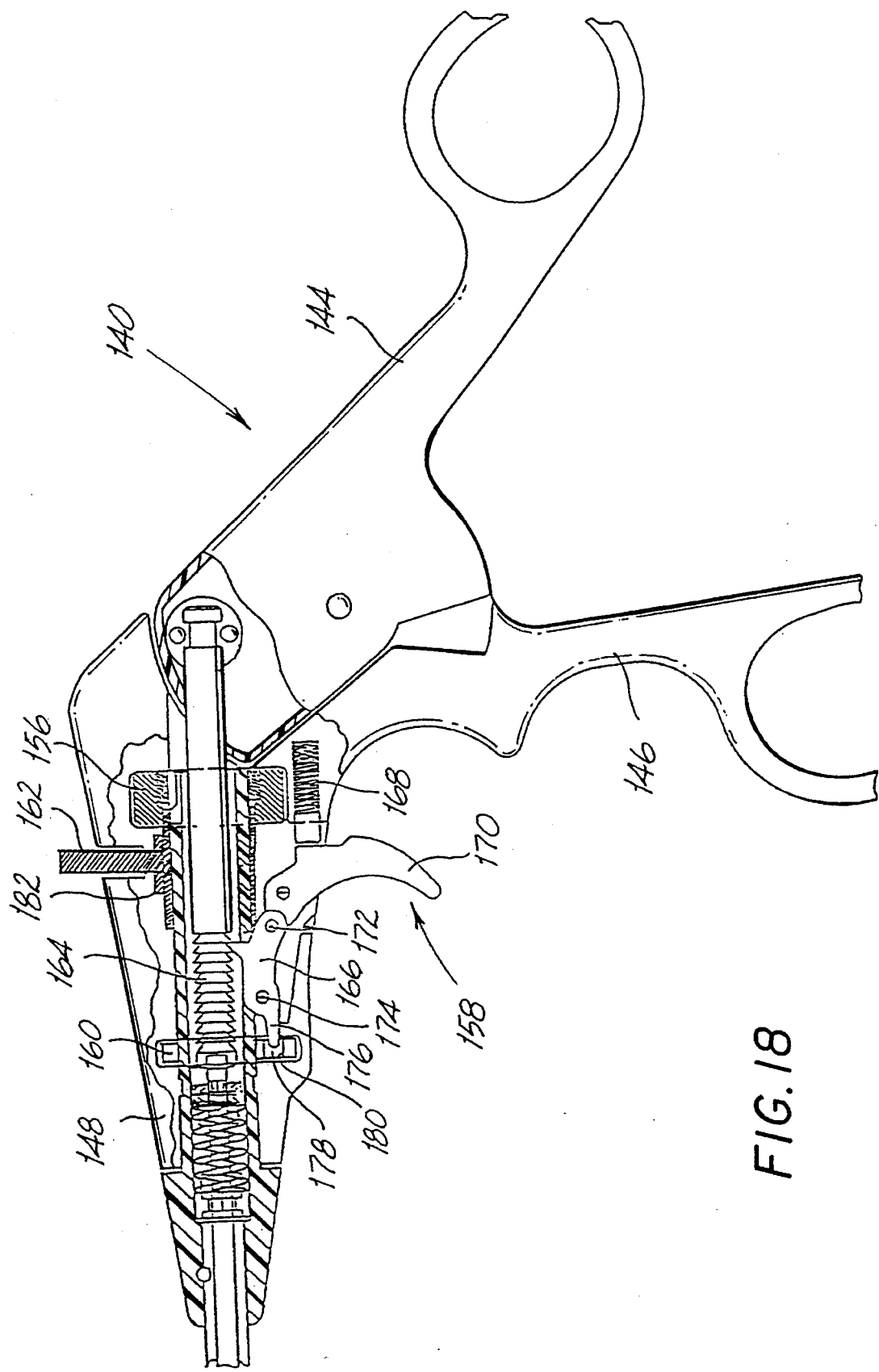
FIG. 18 illustrates a side cut-away view of the device of FIG. 16.
Figure 20:
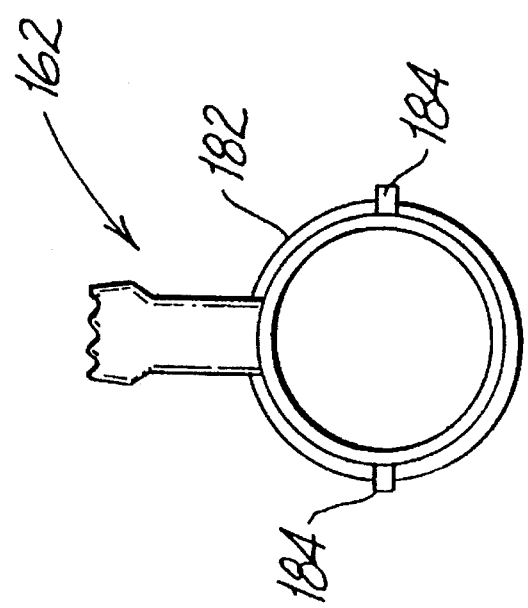
FIG. 20 illustrates a plan view of the stop means for use with the rotation knob of the present invention.

Turning now to FIG. 18, and in view of FIG. 20, ratchet mechanism 158 and actuation means 160 operate in a manner identical to that described above in reference to FIGS. 13–15. Stop means 162 is provided having a body portion 182 surrounding outer tube member 152. Rotation of rotation knob 156 allows for various orientations of the tool mechanism (not shown) which is provided at the distal end of body assembly 150. In order to secure body assembly 150 at a particular orientation, stop means 162 is provided which frictionally engages outer tubular member 152 to lock it in place at the desired orientation. The friction force is applied upon rotation of stop means 162 through the provision of guide posts 184 which travel in tracks provided in barrel portion 148. Guide posts 184 provide a torque to body portion 182 which grips outer tubular member 152 to arrest rotational movement at the desired orientation.

While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. An endoscopic or laparoscopic surgical instrument comprising:

a handle assembly including a barrel portion, a stationary handle and a pivoting handle extending from said barrel portion, said barrel portion having an interior cavity accommodating at least a portion of said pivoting handle;

a body assembly extending distally from said handle assembly and defining a longitudinal axis, said body assembly having a pair of coaxial members including an inner rod member having a proximal end connected to said pivoting handle and mounted to be longitudinally slidable with respect to an outer tube member in response to movement of said pivoting handle, said body assembly terminating at an end remote from said handle assembly in a reciprocatingly movable tool mechanism; and a ratchet mechanism at least partially positioned within said interior cavity of said barrel portion of said handle assembly, said ratchet mechanism being operatively associated with at least one of said pair of coaxial members of said body assembly to provide incremental movement of said tool mechanism with respect to said longitudinal axis of said body assembly.

2. A surgical instrument according to claim 1, wherein said pivotable handle activates said rod member, such that movement of said pivotable handle slidingly reciprocates said rod member within said tube member.

3. A surgical instrument according to claim 1, wherein said ratchet mechanism comprises a rack means positioned on said rod member and a releasable pawl member which engages said rack means to provide for incremental movement of said tool mechanism.

4. A surgical instrument according to claim 3, wherein said rack means comprises a block member secured to said rod member having a plurality of indentations for engaging said pawl member.

5. A surgical instrument according to claim 3, wherein said rack means comprises a series of indentations in said rod member for engaging said pawl member.

6. A surgical instrument according to claim 5, wherein said indentations comprise circumferential notches in said rod member.

7. A surgical instrument according to claim 3, wherein said pawl member includes a trigger member for releasing said ratchet mechanism from engagement with said rack means.

8. A surgical instrument according to claim 3, further comprising actuating means for positioning said pawl member between an engaged position and a disengaged position to allow for incremental movement when said pawl member is engaged and free movement when said pawl member is disengaged.

9. A surgical instrument according to claim 8, wherein said actuating means comprises a pivotable cam member which contacts said pawl member to engage said pawl member with said rack means.

10. A surgical instrument according to claim 8, wherein said pawl member comprises an articulated body portion, terminating in a trigger member at one end and a camming surface at an opposite end, said articulated body pivoting said pawl member out of engagement with said rack means when said camming surface is out of contact with said actuating means, and said body pivoting said pawl member into engagement with said rack means when said camming surface is in contact with said actuating means.

11. A surgical instrument according to claim 10, wherein said articulated body pivots said pawl member out of engagement with said rack means when said camming surface contacts said actuating means, and said body pivoting said pawl member into engagement with said rack means when said camming surface is out of contact with said actuating means.

12. A surgical instrument according to claim 10, wherein said trigger member is spring biased such that said pawl member is biased to an engaged position upon activation of said actuating means.

13. A surgical instrument according to claim 3, wherein said pawl member comprises an articulated body portion including a trigger member and a pawl arm joined to each other by a floating pivot point, said trigger member being spring biased to engage said pawl arm with said rack means.

14. A surgical instrument according to claim 1, wherein said ratchet mechanism is spring biased to a disengaged position.

15. A surgical instrument according to claim 1, wherein said ratchet mechanism is spring biased to an engaged position.

16. A surgical instrument according to claim 1, wherein said ratchet mechanism comprises a rack means positioned on said portion of said pivoting handle within said interior cavity of said barrel portion and a releasable pawl member, said pawl member engaging said rack means to provide for incremental movement of said tool mechanism.

17. A surgical instrument according to claim 16, wherein said rack means is positioned on said pivoting handle at a point within said interior cavity of said barrel portion, said rack means comprising a plurality of notches for engaging said pawl member.

18. A surgical instrument according to claim 16, wherein said pawl member comprises a body portion forming a trigger member, a leaf spring member and a pawl arm, said leaf spring member biasing said pawl arm into engagement with said rack means, said trigger member being actuable to pivot said pawl arm away from said rack means to release said ratchet mechanism.

19. A surgical instrument according to claim 1, wherein said ratchet mechanism comprises a rack means disposed on said body assembly and a trigger actuated pawl member pivotally secured to said barrel portion of said handle assembly for engaging said rack means.

20. A surgical instrument according to claim 19, wherein said rack means comprises a plurality of circumferential notches in said rod member, said notches providing for incremental movement of said rod member in response to movement of said handle assembly at any orientation of said body assembly.

21. A surgical instrument according to claim 19, wherein said pawl member comprises an articulated body portion including a camming member, a pawl arm and a trigger portion, said pawl member being spring biased to engage said pawl arm with said rack means.

22. A surgical instrument according to claim 20, further comprising actuating means for engaging said pawl arm with said rack means, said actuating means including a camming surface for contacting said camming member of said pawl member to pivot said pawl arm into engagement with said rack means.

23. A surgical instrument according to claim 19, wherein said pawl member comprises an articulated body portion including a trigger member and a pawl arm joined to each other by a floating pivot point, said trigger member being spring biased to engage said pawl arm with said rack means.

24. A surgical instrument according to claim 1, wherein said ratchet means comprises a rack means positioned on said pivoting handle and a spring biased pawl member pivotably secured to said barrel portion of said handle assembly.

25. A surgical instrument according to claim 1, further comprising a rotating mechanic, in for rotating said body assembly relative to said handle assembly.

26. A surgical instrument according to claim 25, wherein said rotating mechanism includes a circumferentially disposed knob member positioned on said body assembly and extending outwardly through a slot on said barrel portion of said handle assembly, said knob member providing for rotational movement of said body assembly.

27. A surgical instrument according to claim 26, wherein said knob member further includes a locking means for arresting rotational movement of said body assembly.

28. A surgical instrument according to claim 26, wherein said ratchet mechanism comprises a rack means positioned on said portion of said pivoting handle within said interior cavity of said barrel portion and a releasable pawl member, said pawl member engaging said rack means to provide for incremental movement of said tool mechanism.

29. A surgical instrument according to claim 28, wherein said rack means is positioned on said pivoting handle at a point within said interior cavity of said barrel portion, said rack means comprising a plurality of notches for engaging said pawl member.

30. A surgical instrument according to claim 28, wherein said pawl member comprises a body portion forming a trigger member, a leaf spring member and a pawl arm, said leaf spring member biasing said pawl arm into engagement with said rack means, said trigger member being actuable to pivot said pawl arm away from said rack means to release said ratchet mechanism.

31. A surgical instrument according to claim 28, wherein said knob member further includes a locking means for arresting rotational movement of said body assembly.

32. A surgical instrument according to claim 26, wherein said ratchet mechanism comprises a rack means positioned on said rod member and a releasable pawl member which engages said rack means to provide for incremental movement of said tool mechanism.

33. A surgical instrument according to claim 32, wherein said rack means comprises a plurality of circumferentially disposed indentations in said rod member to provide means for engaging said pawl member during rotation of said body assembly.

34. A handle assembly for endoscopic and laparoscopic surgical instruments, said instrument including a body assembly defining a longitudinal axis and being secured to said handle assembly and having an inner rod member coaxially slidable with respect to said longitudinal axis within an outer tube member, said instrument further including a tool mechanism secured at an end of said body assembly distal from said handle assembly, said handle assembly comprising:

a pivoting handle connected to a proximal end of said inner rod member;

a stationary handle;

a barrel portion supporting said stationary handle and having an interior cavity accommodating at least a portion of said pivoting handle; and a ratchet mechanism at least partially disposed within said interior cavity of said barrel portion of said handle assembly for incrementally moving said tool mechanism with respect to said longitudinal axis of said body assembly.

35. A handle according to claim 34, wherein said ratchet mechanism comprises a pawl mechanism pivotably disposed on said stationary handle and a rack means disposed on said pivoting handle assembly.

36. A handle assembly according to claim 35, wherein said pawl mechanism comprises a leaf spring, a trigger and a pawl arm, leaf spring biasing said pawl arm into engagement with said rack means.

37. A handle assembly according to claim 36, wherein said trigger releases said pawl arm from engagement with said rack means.

38. An endoscopic or laparoscopic surgical instrument comprising:

a handle assembly having an interior cavity and including a barrel portion and at least one pivoting handle;

a body assembly extending from said handle assembly and defining a longitudinal axis, said body assembly having a pair of coaxial members including an inner rod member having a proximal end connected to said at least one pivoting handle and slidable with respect to said longitudinal axis within an outer tube member in response to movement of said at least one pivoting handle, said body assembly terminating at an end remote from said handle assembly in a reciprocatingly movable tool mechanism; and incremental means operatively associated with said pivoting handle positioned at least partially within said interior cavity of said handle assembly for engaging at least one of said pair of coaxial members of said body assembly to provide incremental movement of said tool mechanism with respect to said longitudinal axis in response to movement of said at least one pivoting handle of said handle assembly.

39. A surgical instrument according to claim 38, wherein said means for engaging selectively engages said inner rod member of said body assembly.

40. A surgical instrument according to claim 39, wherein said means for engaging comprises a pawl member which engages a rack member positioned on said inner rod member.

41. A surgical instrument according to claim 38, wherein said means for engaging frictionally engages said inner rod member of said body assembly.

42. A surgical instrument according to claim 38, further comprising a deactivation mechanism for disengaging said incremental means for allowing unrestricted movement of said tool mechanism in response to movement of said at least one handle of said handle assembly.

43. An endoscopic or laparoscopic surgical instrument comprising:

a handle assembly having an interior cavity and at least one pivoting handle;

a body assembly extending distally from said handle assembly and defining a longitudinal axis, said body assembly having a pair of coaxial members including an inner rod member having a proximal end connected to said at least one pivoting handle and slidable with respect to said longitudinal axis within an outer tube member in response to movement of said at least one pivoting handle of said handle assembly, said body assembly terminating at an end remote from said handle assembly in a reciprocatingly movable tool mechanism;

means for providing incremental movement of said tool mechanism substantially housed within said interior cavity of said handle assembly; and means for moving said incremental movement means between an operable and an inoperable position, said incremental movement means providing for incremental movement of said tool mechanism with respect to said longitudinal axis when in said operable position and unrestricted movement of said tool mechanism with respect to said longitudinal axis when in said inoperable position.

44. A surgical instrument according to claim 43, wherein said incremental movement means comprises a ratchet mechanism.

45. An apparatus comprising:

a handle assembly having an interior cavity and at least one pivoting handle;

an endoscopic portion defining a longitudinal axis and extending from said handle assembly;

a tool mechanism extending from a distal end of said endoscopic portion and movable between open and closed positions with respect to said longitudinal axis;

said handle assembly including a ratchet mechanism for allowing incremental movement of said tool mechanism, at least a portion of said ratchet mechanism being mounted within said interior cavity of said handle assembly; and means for deactivating said ratchet mechanism for allowing unrestricted movement of said tool mechanism between said open and said closed positions.

46. An apparatus according to claim 45, wherein said deactivating means comprises a lever movable from a first position to a second position.

47. An apparatus according to claim 45, wherein said handle assembly further comprises a stationary handle, said ratchet mechanism comprising a rack connected to one of said stationary handle and said pivoting handles and a pawl connected to said other handle.

48. An apparatus according to claim 47, wherein said rack is connected to said pivoting handle and said pawl is connected to said stationary handle.

49. An apparatus according to claim 47, wherein said pawl is movable from a first position engaged with said rack to a second position disengaged from said rack.

50. An apparatus according to claim 49, wherein said deactivating means moves said pawl between said first and second positions.

51. An apparatus according to claim 50, further comprising means for rotating said endoscopic portion with respect to said handle assembly.

52. An apparatus according to claim 51, wherein at least a portion of said rotating means is positioned on said handle assembly.

53. An apparatus according to claim 50, wherein said rack comprises a plurality of teeth positioned substantially parallel to the longitudinal axis of the endoscopic portion.

54. An apparatus according to claim 53, wherein said direction of movement of said pawl between said first and second positions is substantially perpendicular to the longitudinal axis of the endoscopic portion.

55. An apparatus according to claim 47, wherein substantially the entire portion of said rack or said pawl are mounted within said interior cavity of the handle assembly.

56. An apparatus according to claim 47, wherein said deactivating means is connected to said stationary handle.

57. An apparatus according to claim 56, wherein said deactivating means comprises a finger operable pivoting member.

58. An apparatus according to claim 45, wherein said handle assembly is positioned at a proximal end of said endoscopic portion.

* * * * *